United States Patent [19]
Batal et al.

[11] Patent Number: 5,045,223
[45] Date of Patent: Sep. 3, 1991

[54] N-SULFONYLOXAZIRIDINES AS BLEACHING COMPOUNDS

[75] Inventors: David J. Batal, Secaucus, N.J.; Stephen A. Madison, Valley Cottage, N.Y.

[73] Assignee: Lever Brothers Company, Division of Conopco, Inc., New York, N.Y.

[21] Appl. No.: 494,709

[22] Filed: Mar. 16, 1990

[51] Int. Cl.$^5$ .................. C11D 3/395; C11D 7/54; D06L 3/02

[52] U.S. Cl. ........................... 252/102; 8/110; 8/111; 8/115.51; 252/8.7; 252/90; 252/94; 252/95; 252/173; 252/174; 252/174.12; 252/186.21; 252/186.22; 252/186.44; 252/549

[58] Field of Search ............... 252/102, 94, 95, 186.44

[56] References Cited

U.S. PATENT DOCUMENTS

| | | | |
|---|---|---|---|
| 2,809,937 | 10/1957 | Gray | 252/102 |
| 3,054,753 | 9/1962 | Hurt et al. | 252/102 |
| 3,153,565 | 10/1964 | Dithmar et al. | 252/102 |
| 3,183,266 | 5/1965 | Matzner | 252/102 |
| 3,245,913 | 4/1966 | Matzner | 252/102 |
| 3,948,795 | 4/1976 | Kawabe et al. | 252/99 |
| 4,120,652 | 10/1978 | Scholer et al. | 252/97 |
| 4,123,376 | 10/1978 | Gray | 252/97 |
| 4,128,490 | 12/1978 | Finley et al. | 252/99 |
| 4,164,395 | 8/1979 | Finley et al. | 252/99 |
| 4,167,487 | 9/1979 | Gray | 252/102 |
| 4,169,805 | 10/1979 | Blumkergs et al. | 252/99 |
| 4,300,897 | 11/1981 | Gray | 252/97 |
| 4,412,934 | 11/1983 | Chung et al. | 252/186.38 |

OTHER PUBLICATIONS

"2-Arylsulphonyl-3-Phenyloxaziridines: a New Class of Stable Oxaziridine Derivatives", Davis, Nadir and Kluger, J.C.S. Chem. Comm. 1977, p. 25.

"Synthesis of 2-Sulfonyl-and 2-Sulfamyloxaziridines Using Potassium Peroxymonosulfate (Oxone)", David, Chattopadhyay, Towson, Lal & Reddy, J. Org. Cham., 1988, vol. 53, p. 2087.

"Synthesis and Structure of 2-Arenesulfonyl-3-aryloxaziridines: a New Class of Oxaziridines", Davis, Lamendola, Nadir, Kluger, Sedergran, Panunto, Billmers, Jenkins, Turchi, Watson, Chen and Kimura, J. Amer. Chem. Soc., 1980, vol. 102, p. 2000.

"Selective Catalytic Oxidation of Sulfides to Sulfoxides Using N-Sulfonyloxaziridines", Davis and Lal, J. Org. Chem., 1988, vol. 53, p. 5004.

Vishwakarma, L. C., Stringer, O. D., Davis, F. A., *Org. Synth.* 1987, 66, 203.

"Applications of Oxariridines in Organic Synthesis", Davis, F. A., Sheppard, A. C., *Tetrahedron* 1989, 45, 5703.

"Chemistry of Oxaziridines.2. Improved Synthesis of 2-Sulfonyloxaziridines", Davis, F. A., Stringer, O. D., *J. Org. Chem.*, 1982, 47, 1774.

"1,2-Benzisothiazole 1,1-Dioxides. Synthesis of 3-Alkyl—(or Aryl—), 1,2-Benzisothiazole 1,1-Dioxides and Related Compounds", Abramovitch, R. A., Smith, E. M., Humber, M., Purtschert, B., Srinivasan, P. C., Singer, G. M., *J. Chem. Soc. Perkin I* 1974, 2589.

Primary Examiner—Paul Lieberman
Assistant Examiner—A. Beadles-Hay
Attorney, Agent, or Firm—Milton L. Honig

[57] ABSTRACT

Novel bleaches, a method for bleaching substrates using these materials and detergent compositions containing same are reported. The bleaches are of the N-sulfonyloxaziridine type. Substrates such as fabrics may be bleached in an aqueous solution containing the oxaziridine.

29 Claims, No Drawings

N-SULFONYLOXAZIRIDINES AS BLEACHING COMPOUNDS

BACKGROUND OF THE INVENTION

1. Field of the Invention

The invention relates to novel bleaching compounds, compositions containing same and a method for using these bleaches in detergent compositions, especially for cleaning fabrics.

2. The Related Art

Many household and personal care products are formulated with an active oxygen-releasing material to effect removal of stain and soil. Oxygen-releasing materials have an important limitation; their activity is extremely temperature dependent. Temperatures in excess of 60° C. are normally required to achieve any bleach effectiveness in an aqueous wash system. Especially for cleaning fabrics, high temperature operation is both economically and practically disadvantageous.

The art has partially solved the aforementioned problem through the use of activators. These activators, also known as bleach precursors, often appear in the form of carboxylic acid esters. In an aqueous liquor, anions of hydrogen peroxide react with the ester to generate the corresponding peroxyacid which oxidizes the stained substrate. Commercial application of this incorporating sodium nonanoyloxybenzene sulfonate. This activator is typical of a class that features u phenol sulfonate leaving group; see U.S. Pat. No. 4,412,934 (Chung et al.).

While carboxylic acid ester activators and the like are often effective, these systems are not fully efficient. Relatively large amounts of activator are often necessary. Amounts as high as 8% may be required in a detergent formulation for bleaching fabrics. Cost for these relatively expensive activators is of major concern at such levels.

Outside the context of consumer products, there have been reports of unusually effective oxidizing agents. F. A. Davis and coworkers, in a series of articles, reported preparation of a new class of stable oxidizing agents, namely 2-arenesulfonyl-3-aryloxaziridines. See Davis, Nadir, and Kluger, *J.C.S. Chem. Comm.* 1977, 25; Davis, Lamendola Jr., Nadir, Kluger, Sederjarn, Panunto, Billmers, Jenkins Jr., Turchi, Watson, Chen and Kimura, *J. Amer. Chem. Soc.* 1980, 102, 2000; and Davis, Chattopadhay, Towson, Lal and Reedy, *J. Org. Chem.* 1988, 53, 2087. These oxaziridines were prepared by peracid or monopersulfate oxidation of a corresponding sulfonimine under alkaline conditions. In late 1988, Davis published a paper entitled "Selective Catalytic Oxidation of Sulfides to Sulfoxides Using N-sulfonyloxaziridines", *J. Org. Chem.* 1988, 53, 5004. Therein described is a system where sulfonimine reacts with monopersulfate to generate an in situ oxaziridine in a toluene-water biphasic mixture. Oxaziridine then coverts the sulfide to a sulioxide and generates starting sulfonimine, thereby rendering the process catalytic in nature. Beyond use as a synthetic tool, there is no suggestion of any possible application for N-sulfonyloxaziridine chemistry to the problem of removing stain in consumer applications, such as in cleaning fabrics.

It is an object of the present invention to provide novel bleaches and detergent compositions containing such bleaches that operate over a wide temperature range including that of under 60° C.

It is another object of the present invention to provide novel bleaches which are effective at relatively low concentrations thereby achieving a quite cost effective stain removal system.

A further object of the present invention is to provide a method for bleaching stained substrates such us clothes, household hard surfaces including sinks, toilets and the like, and even dentures.

Other objects of the present invention will become apparent through the following summary, detailed discussion and examples.

SUMMARY OF THE INVENTION

A bleaching composition is provided comprising:

(i) from about 0.05 to about 10% of an oxygen transfer agent whose structure is:

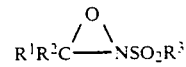

wherein:

$R^1$ may be a substituted or unsubstituted radical selected from the group consisting of hydrogen, phenyl, aryl, heterocyclic ring, alkyl and cycloalkyl radicals;

$R^2$ may be a substituted or unsubstituted radical selected from the group consisting of hydrogen, phenyl, aryl, heterocyclic ring, alkyl, cycloalkyl,

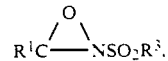

nitro, halo, cyano, alkoxy, keto, carboxylic and carboalkoxy radicals;

$R^3$ may be a substituted or unsubstituted radical selected from the group consisting of phenyl, aryl, heterocyclic ring, alkyl, cycloalkyl, nitro, halo, and cyano radicals;

$R^1$ with $R^2$ and $R^2$ with $R^3$ may respectively together form a cycloalkyl, heterocyclic, and aromatic ring system; and (ii) from about 0.5 to 50% of a surfactant.

Additionally, there is provided a method for bleaching a stained substrate comprising the step of applying to the stained substrate an aqueous solution comprising an oxygen transfer agent whose structure is

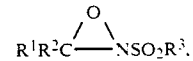

with radical groups as defined above.

Certain novel compounds are also provided whose structure is

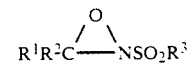

having radical groups as defined above, with the proviso that at least one of $R^1$, $R^2$, $R^3$ is substituted with a water-solubilizing functional group. Typical water-solubilizing groups include carboxylic acid, phosphoric acid, phosphonic acid, sulfuric acid, sulfonic acid, and, especially, their salt derivatives.

DETAILED DESCRIPTION

It has been found that N-sulfonyloxaziridines can operate as bleaches to transfer active oxygen to stairs.

Consumer and industrial articles can effectively be bleached to remove stains present on such articles.

N-Sulfonyloxaziridines covered by the present invention are those whose structure is:

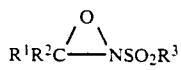

wherein $R^1$ may be a substituted or unsubstituted radical selected from the group consisting of hydrogen, phenyl, aryl, heterocyclic ring, alkyl, and cycloalkyl radicals;

$R^2$ may be a substituted or unsubstituted radical selected from the group consisting of hydrogen, phenyl aryl, heterocyclic ring, alkyl, cycloalkyl,

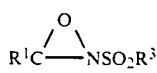

nitro, halo, cyano, alkoxy, keto, carboxylic, and carboalkoxy radicals;

$R^3$ may be a substituted or un substituted radical selected from the group consisting of phenyl, or aryl, heterocyclic ring, alkyl, cycloalkyl, nitro, halo, and cyano radicals; and $R^1$ with $R^2$ and $R^2$ and $R^3$ may respectively together form a cycloalkyl, heterocyclic or aromatic ring system.

Often advantageous are N-sulfonyloxaziridines having at least one of $R^1$, $R^2$, $R^3$ substituted with a water-solubilizing functional group. These functional groups may be selected from carboxylates, phosphates, phosphonates, sulfates, sulfonates in acid or salt form. Suitable salts include those whose counterions are selected from alkali metal, ammonium, and $C_2$–$C_6$ alkanolammonium anions.

Amine functional groups may also be incorporated into $R^1$, $R^2$ or $R^3$ to provide water-solubilization of the N-sulfonyloxaziridines. An example combining the amine and heterocyclic structure is that of pyridine.

A water-solubilizing functional group is one which renders the N-sulfonyloxaziridines soluble to the extent of at least 2 mg/l, preferably at least 25 mg/l, optimally at least 250 mg/l in water at 25° C.

Heterocyclic rings according to this invention include cycloaliphatic and cycloaromatic type radicals incorporating an oxygen, sulfur and/or nitrogen atom within the ring system. Representative nitrogen heterocycles include pyridine, morpholine, pyrrole, imidazole, triazole, tetrazole, pyrrolidine, piperidine and piperazine. Suitable oxygen heterocycles include furan, tetrahydrofuran and dioxane. Sulfur heterocycles may include thiophene and tetrahydrothiophene. Along the various heterocycles, it has been found that those incorporating nitrogen are the most active.

The term "substituted" is defined in relation to $R^1$, $R^2$, $R^3$ as a substituent which is a nitro, halo, cyano, $C_1$–$C_{20}$ alkyl, amino, aminoalkyl, thioalkyl, sulfoxyalkyl, carboxyester, hydroxy, $C_1$–$C_{20}$ alkoxy, polyalkoxy and $C_1$–$C_{40}$ quaternary di- or tri- alkylammonium function.

Novel N-sulfonyloxaziridine compounds are described below wherein $R^1$ is hydrogen, $R^2$ is phenyl with an X substituent, and $R^3$ is phenyl with a Y substituent. Very often, X and Y groups are water-solubilizing groups, most preferably being carboxylic acid or salts thereof. Representative structures are as follows:

$$\text{X-PhCH}\underset{\diagdown O \diagup}{-}\text{NSO}_2\text{Ph-Y}$$

| | X | Y |
|---|---|---|
| OX 1 | 4-CO$_2$H | 4-Cl |
| OX 2 | 4-CO$_2$H | H |
| OX 3 | 4-Cl | 4-CO$_2$H |
| OX 4 | H | 4-CO$_2$H |
| OX 5 | 4-CO$_2$H | 4-CO$_2$H |
| OX 6 | 4-CO$_2$H | 3-NO$_2$ |
| OX 7 | 4-CN | 4-CO$_2$H |
| OX 8 | 4-OMe | 4-CO$_2$H |
| OX 9 | 3-OH | 4-Cl |

OX 10

$$\begin{array}{c}\text{NSO}_2\text{Ph-p-CO}_2\text{H}\\ \diagup O \\ \diagdown \text{CH} \\ \vert \\ \text{C}_6\text{H}_4 \\ \vert \\ \text{HC} \\ \diagdown O \\ \diagup \\ \text{HO}_2\text{C-p-PhSO}_2\text{N}\end{array}$$

Additional N-sulfonyloxaziridines which have been found useful and have been synthesized are those with the structures listed below:

$$\text{Ar}^1\text{CH}\underset{\diagdown O \diagup}{-}\text{NSO}_2\text{Ar}$$

| | Ar$^1$ | Ar |
|---|---|---|
| OX 11 | Ph | Ph |
| OX 12 | 4-NO$_2$Ph | Ph |
| OX 13 | 4-ClPh | 4-ClPh |
| OX 14 | 4-MeSOPh | Ph |
| OX 15 | 3-Pyr | Ph |

OX 16

(benzisothiazole structure with Bu substituent, O, N, SO$_2$)

The following further compounds are illustrative of N-sulfonyloxaziridines within the present invention.

2-Benzenesulfonyl-3-(methylsulfonylphenyl)oxaziridine
2-Benzenesulfonyl-3-(2-pyridinyl)oxaziridine
2-Benzenesulfonyl-3-(4-pyridinyl)oxaziridine
2-(4-Chlorobenzenesulfonyl)-3-(pyridinyl)oxaziridine
2-(3-Pyridinyl)-3-phenyloxaziridine
2-Benzenesulfonyl-3-(N-methyl-3-pyridinyl)oxaziridine chloride salt
1,2-Benzisothiazole-1,1-dioxide oxide
3-Trimethylammoniomethyl-1,2-benzisothiazole-1,1-dioxide oxide chloride salt
2-Benzenesulfonyl-3-(4-trimethylammoniophenyl)oxaziridine chloride salt
2-Benzenesulfonyl-3-(4-cholyloxycarbonylphenyl)oxaziridine chloride salt 2-(4-Cholyloxycarbonylbenzenesulfonyl)-3-phenyloxaziridine chloride salt
2-Benzenesulfonyl-3-(4-sulfoethylcarbonylphenyl)oxaziridine chloride salt
2-Benzenesulfonyl-3-methyl-3-phenyloxaziridine
2-Benzenesulfonyl-3,3-dimethyloxaziridine
2-Toluenesulfonyl-3-carbomethoxyoxaziridine
2-Toluenesulfonyl-3-carboxyoxaziridine sodium salt
2-Methanesulfonyl-3-phenyloxaziridine
2-Methanesulfonyl-3-(4-carboxyphenyl)oxaziridine The foregoing oxygen transfer agents may be incorporated into detergent compositions optionally along with further bleaching components such as a peroxygen compound capable of yielding peroxide anion in an aqueous solution and a bleach precursor.

Amounts of oxygen transfer agent suitable for the present invention may range from about 0.05 to 10%, preferably from about 0.2 to 5% by weight of the composition.

The peroxygen compound may be present from about 1 to 60%, preferably from about 1% 25% by weight of the composition.

The molar ratio of peroxide anion (or a peroxygen compound generating the equivalent amount of peroxide anion) to oxygen transfer agent will range from about 1500:1 to 1:2, preferably about 150:1 to 1:1, optimally between about 25:1 to 2:1.

Peroxide anion sources are well known in the art. They include the alkali metal peroxides, organic peroxides such as urea peroxide, and inorganic persalts, such as the alkali metal perborates, percarbonates, perphosphates, persilicates and persulfates. Mixtures of two or more such compounds may also be suitable. Particularly preferred are sodium perborate tetrahydrate and, especially, sodium perborate monohydrate. Sodium perborate monohydrate is preferred because it has excellent storage stability while also dissolving very quickly in aqueous solutions.

Alkylhydroperoxides are another suitable class of peroxygen compounds. Examples of these materials include cumene hydroperoxide and t-butyl hydroperoxide.

Organic peroxy acids may also be suitable as the peroxygen compound. Such materials have a general formula:

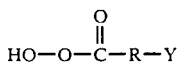

wherein R is an alkylene or substituted alkylene group containing from 1 to about 22 carbon atoms or a phenylene or substituted phenylene group, and Y is hydrogen, halogen, alkyl, aryl or

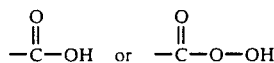

The organic peroxy acids usable in the present invention can contain either one or two peroxy groups and can be either aliphatic or aromatic. When the organic peroxy acid is aliphatic, the unsubstituted acid has the general formula:

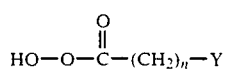

where Y can be, for example, H, CH$_3$, CH$_2$Cl, COOH, or COOOH; and n is an integer from 1 to 20.

When the organic peroxy acid is aromatic, the unsubstituted acid has the general formula:

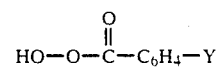

wherein Y is hydrogen, alkyl, alkylhalogen, halogen, or COOH or COOOH.

Typical monoperoxy acids useful herein include alkyl peroxy acids and aryl peroxy acids such as: wherein R is an alkylene or substituted alkylene group containing from 1 to about 22 carbon atoms or a phenylene or substituted phenylene group, and Y is hydrogen, halogen, alkyl, aryl or

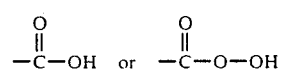

The organic peroxy acids usable in the present invention can contain either one or two peroxy groups and can be either aliphatic or aromatic. When the organic peroxy acid is aliphatic, the unsubstituted acid has the general formula:

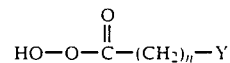

where Y can be, for example, H CH$_3$, CH$_2$Cl COOH, or COOOH; and n is an integer from 1 to 20.

When the organic peroxy acid is aromatic, the unsubstituted acid has the general formula:

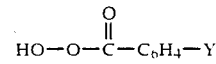

where Y is hydrogen, alkyl, alkylhalogen, halogen, or COOH or COOOH.

Typical monoperoxy acids useful herein include alkyl peroxy acids and aryl peroxy acids such as:

Advantageously a bleach precursor is utilized in combination with the peroxide anion source, especially where the source is an inorganic peroxide such as sodium perborate or sodium percarbonate. The bleach precursor is defined as a material that reacts with peroxide anion and forms therewith a peracid, percarbonic acid or perimidic acid. Precursors of this invention are water-soluble materials, being soluble generally to an extent of at least 1%, preferably at least about 5% by weight at 25° C. and pH 7. Certain precursors of this invention may further be defined by the Per-Acid Formation Test wherein the precursor will have a titre of at least 1.5 ml of 0.1N sodium thiosulphate. This test may be found in U.S. Pat. No. 3,177,148 (Bright et al) herein incorporated by reference.

Precursors which may be utilized for purposes of the present invention include:

(a) N-diacylated and N,N'-polyacylated amines, such as N,N,N',N'-tetraacetyl methylene diamine and N,N,N',N'-tetraacetyl ethylene diamine, N,N-diacetylaniline, N,N-diacetyl-p-toluidine; 1,3-diacylated hydantoins such as, for example, 1,3-diacetyl-5, 5-dimethyl hydantoin and 1,3-dipropionyl hydantoin;

acetoxy(N,N,N')-polyacylmalonamide, for example acetoxy-(N,N')-diacetylmalonamide;

(b) Diacylated 2,5-diketopiperazine, such as 1,4-diacetyl-2,5-diketopiperazine, 1,4-dipropionyl -2,5-diketopiperazine and 1,4-dipropionyl-3,6-dimethyl-2,5-diketopiperazine;

(c) Acylation products of propylenendlurea or 2,2-dimethylpropylenediurea (2,4,6,8-tetraaza-bicyclo-(3,3,1)-nonane-3,7-dione or its 9,9-dimethyl derivative), especially the tetraacetyl- or the tetrapropionyl-propylenediurea or their dimethyl derivatives;

(d) Carbonic acid esters, for example the sodium salts of p-(ethoxycarbonyloxy)-benzoic acid and p-(propoxycarbonyloxy)-benzenesulphonic acid;

(e) Acyloxy-(N,N')polyacyl malonamides, such as alpha-acetoxy(N,N')diacetyl malonamide; and (f) Quaternary ammonium substituted paroxycarbonic or carboxylic acid esters such as 2-(N,N,N-trimethylammonium) ethyl sodium 4-sulphophenyl carbonate.

The precursors which are of special interest are N,N,N,'N'-tetraacetyl-ethylene-diamine (TAED), tetraacetyl-glycoluril (TAGU), glucose pentaacetate, xylose tetraacetate, sodium acetyloxybenzene sulfonate (SABS) and sodium nonanoyloxybenzene sulfonate (SNOBS).

Bleach systems of the present invention may be employed for a wide variety of purposes, but are especially useful in the cleaning of laundry. When intended for such purpose, the peroxygen compound and oxygen transfer agent of the present invention will usually also be combined with surface-active materials, detergency builders and other known ingredients of laundry detergent formulations.

The surface-active material may be naturally derived, or synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch. The total level of the surface-active material may range up to 50% by weight, preferably being from about 0.5 to 40% by weight of the composition, most preferably 4 to 25%.

Synthetic anionic surface-actives are usually water-soluble alkali metal salts of organic sulphates and sulphonates having alkyl radicals containing from about 8 to about 22 carbon atoms.

Examples of suitable synthetic anionic detergent compounds are sodium and ammonium alkyl sulphates, especially those obtained by sulphating higher ($C_8$–$C_{18}$) alcohols produced for example from tallow or coconut oil; sodium and ammonium alkyl ($C_9$–$C_{20}$) benzene sulphonates, sodium alkyl glyceryl ether sulphates, especially those ethers of the higher alcohols derived from tallow or coconut oil and synthetic alcohols derived from petroleum; sodium coconut oil fatty acid monoglyceride sulphates and sulphonates; sodium and ammonium salts of sulphuric acid esters of higher ($C_9$–$C_{18}$) fatty alcohol-alkylene oxide, particularly ethylene oxide, reaction products; the reaction products of fatty acids such as coconut fatty acids esterified with isethionic acid and neutralized with sodium hydroxide; sodium and ammonium salts of fatty acid amides of methyl taurine; alkane monosulphonates such as those derived by reacting alpha-olefins ($C_8$–$C_{20}$) with sodium bisulphite and those derived by reacting paraffins with $SO_2$ and $Cl_2$ and then hydrolyzing with a base to produce a random sulphonate; sodium and ammonium $C_7$–$C_{12}$ dialkyl sulfosuccinates; and olefin sulphonates, which term is used to describe the material made by reacting olefins, particularly $C_{10}$–$C_{20}$ alpha-olefins, with $SO_3$ and then neutralizing and hydrolyzing the reaction product. The preferred anionic detergent compounds are sodium ($C_{11}$–$C_{15}$) alkylbenzene sulphonates, sodium ($C_{16}$–$C_{18}$) alkyl sulphates and sodium ($C_{16}$–$C_{18}$) alkyl ether sulphates.

Examples of suitable nonionic surface-active compounds which may be used, preferably together with the anionic surface-active compounds, include in particular the reaction products of alkylene oxides, usually ethylene oxide, with alkyl ($C_6$–$C_{22}$) phenols, generally 5–25 EO, i.e. 5–25 units of ethylene oxide per molecule; the condensation products of aliphatic ($C_8$–$C_{18}$) primary or secondary linear or branched alcohols with ethylene oxide, generally 2–30 EO, and products made by condensation of ethylene oxide with the reaction products of propylene oxide and ethylene diamine. Other so-called nonionic surface-actives include alkyl polyglycosides, long chain tertiary amine oxides, long chain tertiary phosphine oxides and dialkyl sulphoxides.

Amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

Soaps may also be incorporated into the compositions of the invention, preferably at a level of less than 30% by weight. They are particularly useful at low levels in binary (soap/anionic) or ternary mixtures together with nonionic or mixed synthetic anionic and nonionic compounds. Soaps which are used are preferably the sodium, or less desirably potassium, salts of saturated or unsaturated $C_{10}$–$C_{24}$ fatty acids or mixtures thereof. The amount of such soaps can be varied between about 0.5% and about 25% by weight, with lower amounts of about 0.5% to about 5% being generally sufficient for lather control. Amounts of soap between about 2% and about 20%, especially between about 5% and about 15%, are used to give a beneficial effect on detergency. This is particularly valuable in compositions used in hard water when the soap acts as a supplementary builder.

The detergent compositions of the invention will normally also contain a detergency builder. Builder materials may be selected from (1) calcium sequestrant materials, (2) precipitating materials, (3) calcium ion-exchange materials and (4) mixtures thereof.

In particular, the compositions of the invention may contain any one of the organic or inorganic builder materials, such as sodium or potassium tripolyphosphate, sodium or potassium pyrophosphate, sodium or potassium orthophosptate, sodium carbonate, the sodium salt of nitrilotriacetic acid, sodium citrate, carboxymethylmalonate, carboxymethyloxysuccinate, tartrate mono- and di- succinates, oxydisuccinate, crystalline or amorphous aluminosilicates and mixtures thereof.

Polycarboxylic homo- and co-polymers may also be included as builders and to function as powder structurants or processing aids. Particularly preferred are polyacrylic acid (available under the trademark Acrysol from the Rohm and Haas Company) and acrylic-maleic acid copolymers (available under the trademark Sokalan from the BASF Corporation) and alkali metal or other salts thereof.

These builder materials may be present at a level of, for example, from about 1 to 80% by weight, preferably from 10 to 60% by weight.

Upon dispersal in a wash water, the initial amount of peroxygen compound, when present, should range anywhere from about 0.05 to about 250 ppm active oxygen per liter of water, preferably between about 1 to 50 ppm. Within the wash media the amount of oxygen transfer agent initially present should be from about 0.01 to about 300 ppm, preferably from about 5 to 100 ppm. Surfactant, when present, should be available in the wash water from about 0.05 to 1.0 grams per liter, preferably from 0.15 to 0.40 grams per liter. When present, the builder amount will range from about 0.1 to 3.0 grams per liter.

Apart from the components already mentioned, the detergent compositions of the invention can contain any of the conventional additives in the amounts in which such materials are normally employed in detergent compositions. Examples of these additives include lather boosters such as alkanolamides, particularly the monoethanolamides derived from palmkernel fatty acids and coconut fatty acids, lather depressants such as alkyl phosphates and silicones, anti-redeposition agents such as sodium carboxymethylcellulose and alkyl or substituted alkylcellulose ethers, stabilizers such as ethylene diamine tetraacetic acid and phosphonic acid derivatives (Dequest®), fabric softening agents, inorganic salts such as sodium sulphate, and, usually present in very small amounts, fluorescent agents, perfumes, enzymes such as proteases, cellulases, lipases and amylases, germicides and colorants.

The oxygen transfer agents may be useful for removing stains both in consumer type products and for industrial applications. Among consumer products incorporating this invention are laundry detergents, laundry bleaches, hard surface cleaners, toilet bowl cleaners, automatic dishwashing compositions and even denture cleaners. Stained consumer products benefiting from treatment with compositions of this invention may include clothes and other fabrics; household fixtures and appliances such as sinks, toilet bowls and oven ranges; tableware such as drinking glasses, dishes, cookware and utensils; and even dentures. Hair colorants may also be formulated with the bleach composition of this invention. The bleaching system of this invention may also be applied to industrial uses such as for the bleaching of wood pulp.

The system of the present invention may be delivered in a variety of product forms including powders, on sheets or other substrates, in pouches, in tablets, in aqueous liquids or in non-aqueous liquids such as liquid nonionic detergents.

The following examples will more fully illustrate the embodiments of this invention. All parts, percentages and proportions referred to herein and in the appended claims are by weight unless otherwise illustrated.

EXAMPLE 1

Synthesis of N-Sulfonyloxaziridines

The N-sulfonyloxaziridines used for the present invention were synthesized by oxidizing the corresponding N-sulfonimines with 3-chloroperoxybenzoic acid (MCPBA) in a mixture of chloroform and aqueous sodium bicarbonate. The starting sulfonimines were prepared by heating equivocal amounts of the requisite aromatic aldehydes and sulfonamides in toluene containing a catalytic amount of p-toluenesulfonic acid (TsOH). The sulfonimine and oxaziridine syntheses were conducted by modifying known literature procedures as set forth by Davis et al. In the sulfonimine syntheses, vessels were either fitted with a drying tube (calcium sulfate) or with a nitrogen flow system. Any water formed from these condensations was removed by equipping the reaction vessels with a Soxhlet extractor containing 3A molecular sieves. Formation of product sulfonimines or N-sulfonyloxaziridines were monitored by TLC and $^1$H NMR analyses. Specific syntheses are outlined in the following examples which focus upon product yield and spectroscopic analyses.

EXAMPLE 2

N-(4-Chlorobenzylidene)-4-chlorobenzenesulfonamide

A stirred solution consisting of 7.03 g (5.0 mmol) of 4-chlorobenzaldehyde, 9.58 g (5.0 mmol) of 4-chlorobenzenesulfonamide, 8 g of 4A molecular sieves and 0.1 g of Amberlite IR-120 in 90 mL of toluene was heated to reflux. The reaction vessel was fitted with a Dean Stark trap which was filled with 4A molecular sieves. The mixture was heated for 4 hours, at which point TLC analysis showed conversion to sulfonimine. The mixture was allowed to cool to room temperature and was filtered. Concentration of the filtrate and subsequent recrystallization of the crude product from $CHCl_3$-hexane gave 7.84 g (50%) of sulfonimine as a white crystalline material: IR 3090, 1598, 1582, 1553, 1321, 1084 $cm^1$; $^1$H NMR ($CDCl_3$, TMS, 60 MHz) δ 9.02 (s, 1), 7.73 (A2B2, 4, $\Delta V = 24$ Hz, $J_{AB} = 8$ Hz), 7.67 (A2B2, 4, $\Delta V = 23$ Hz, $J_{AB} = 9$ Hz); m.p. 128.0 °C.

2-(4-Chlorobenzenesulfonyl)-3-(4-chlorophenyl)oxaziridine (OX 13)

To a vigorously stirred solution (Morton flask) of 1.00 g (3.2 mmol) of the above sulfonimine and 0.06 g (0.11 eq) of benzyltrimethylammonium chloride in 15 mL of $CHCl_3$ and 15 mL of saturated $NaHCO_3$ solution at 0° C. was added a solution of 0.75 g (1.1 eq) of 80% MCPBA (Aldrich) in 10 mL of $CHCl_3$ dropwise over a period of 15 minutes. The mixture was stirred at 0° C. for 0.5 hours. The chloroform layer was separated, washed with water, 10% $NaHSO_3$ (2x), saturated $NaHCO_3$, brine, dried ($MgSO_4$) and concentrated to afford a yellow solid. Trituration under methanol provided 0.83 g (79%) of OX 13 as a white solid: $^1$H NMR ($CDCl_3$, TMS, 60 MHz) δ7.78 (A2B2, 4, $\Delta V = 21$ Hz, $J_{AB} = 8$ Hz), 7.38 (s, 4), 5.48 (s, 1).

EXAMPLE 3

N-(Methylthiobenzylidene)benzenesulfonamide

A stirred mixture consisting of 2.60 g (17.2 mmol) of 4-methylthiobenzaldehyde, 2.70 g (17.2 mmol) of benzenesulfonamide and 20 mg of p-toluenesulfonic acid monohydrate in 150 mL of toluene was heated to reflux. The reaction vessel was equipped with a Soxhlet extractor containing 4A molecular sieves. After heating 8 hours, the mixture was allowed to cool to room temperature and was concentrated to afford 4.60 g (92%) of sulfonimine as light tan crystals: mp 1.50°-155° C.; $^1$H NMR ($CDCl_3$, TMS ext std) δ9.15 (s, 1), 8.27-7.18 (m, 9), 2.53 (s, 3).

2-Benzenesulfonyl-3-(4-methylsulfinylphenyl)oxaziridine (OX 14)

In a 500-ml Morton flask were placed 2.00 g (7 mmol) of the above sulfonimine and 0.14 g (0.11 eq) of benzyltrimethylammonium chloride (BTMAC) in 40 mL of chloroform and 40 mL of saturated $NaHCO_3$ solution. The mixture was cooled to 0° C. and stirred vigorously while a solution of 5.23 g (2.2 eq oxidant) of 50% MCPBA in 40 mL of chloroform was added dropwise. The addition time was 0.5 hours. Stirring was continued an additional 15 minutes and the chloroform layer was separated. The organic phase was washed with water, 10% $NaHSO_3$ solution, saturated $NaHCO_3$ solution, brine and was dried ($MgSO_4$) Concentration gave 1.85 g (84%) of OX 14, a white crystalline material: mp 115°–118 ° C.; $^1H$ NMR ($CDCl_3$, TMS ext std) $\delta 8.33-7.25$ (m, 9), 5.83 (s, 1), 3.25 (s, 3); MS (chemical ionization, isobutane) $m/e$ 324 (M+1), 200, 184, 158, 143, 125.

EXAMPLE 4

N-(3-Pyridinylmethylene)benzenesulfonamide

A stirred mixture consisting of 4.00 g (37 mmol) of 3-pyridinecarboxaldehyde, 5.88 g (37 mmol) of benzenesulfonamide and 20 mg of p-toluenesulfonic acid monohydrate in 120 mL of toluene was heated to reflux under a blanket of nitrogen. The reaction vessel was equipped with a Soxhlet extractor containing 4A molecular sieves. After heating 18 hours, the mixture was allowed to cool to approximately 40° C. and was filtered to remove colored impurities. Addition of hexane to the filtrate led to precipitation of a white solid. Filtration provided 9.10 g (73%) of sulfonimine: mp 123° C.; IR (Nujol) 1640, 1605, 1585, 1560, 1300, 1280, 1220, 860 $cm^{-1}$; $^1H$ NMR ($CDCl_3$, TMS, 60 MHz) $\delta 9.15$ (s, 1), 8.9–8.7 (m, 2), 8.4–7.4 (m, 7).

2-Benzenesulfonyl-3-(3-pyridinyl)oxaziridine (OX 15)

In a 500-mL Morton flask were placed 1.50 g (6.1 mmol) of the above sulfonimine and 0.12 g (0.11 eq) of HTMAC in 40 mL of chloroform and 50 mL of satd $NaHCO_3$ solution. The mixture was cooled to −15° C. chloroform and 50 mL of satd $NaHCO_3$ solution. The mixture was cooled to −15° C. and stirred vigorously while a solution of 6.31 g (3 eq oxidant) of 50% MCPBA in 40 mL of chloroform was added rapidly. The chloroform layer was immediately separated. The organic phase was washed with 30 mL of saturated $NaHSO_3$ solution (2x), 30 mL of satd $NaHCO_3$ solution (3x), brine and was dried to formation of a precipitate. Filtration gave 0.50 g (31%) of OX 15 as a white crystalline solid: mp 79°–80° C.; IR 1590, 1575, 1255, 1160, 1085 $cm^{-1}$; $^1H$ NMR (60 $MH_z$, $CDCl_3$, TMS) $\delta 8.6$ (s, 2), 8.3–7.3 (m, 7), 5.5 (s, 1).

EXAMPLE 5

3-Butyl-1,2-benzisothiazole-1,1-dioxide

This material was prepared by adding 2 equivalents of butyllithium to saccharin in THF at −78° C., followed by aqueous workup at pH 9 as described in the literature by Abramovitch et al., *J. Chem. Soc. Perkin I*, 1974, 2589.

3-Butyl-1,2-benzisothiazole-1,1-dioxide Oxide (OX 16)

In a 500-mL Morton flask were placed 1.00 g (4.5 mmol) of the saccharin derived sulfonimine and 92 mg (0.11 eq) of BTMAC in 40 mL of chloroform and 40 mL of saturated $NaHCO_3$ solution. The mixture was cooled to 0° C. and stirred vigorously while a solution of 1.70 g (1.1 eq oxidant) of 50% MCPBA in 40 mL of chloroform was added dropwise. The addition time was 0.5 hours. Stirring was continued an additional 1.5 minutes and the chloroform layer was separated. The organic phase was washed with 10% $Na_2SO_3$ solution, water, brine and was dried (2x, $K_2CO_3$) Concentration (rotary evaporation followed by hi-vac at 1 torr overnight) gave 0.99 g (93%) of OX 17 as a clear, colorless liquid: IR 3082, 1443, 1358, 1184, 775, 733 $cm^{-1}$; NMR ($CDCl_3$, TMS) $\delta 7.73$ (s, 4), 2.9–2.2 (m, 2), 1.8–1.2 (m, 4), 0.94 (t, 3). Compound OX 17 liberated iodine from potassium iodide-starch test paper.

EXAMPLE 6

Fabric Bleaching By Oxaziridines (general)

Stain bleaching experiments were conducted in a Terg-O-Tometer in 500 mL of milli-Q water using two tea-stained cotton cloths measuring 3×4 inches. In a typical test, 0.75 g of P-Surf ® was added to the system and the pH of the solution was constantly buffered to the indicated level by the addition of dilute aqueous sodium hydroxide or hydrochloric acid. Washes were carried out at 40° C. for 15 minutes.

The oxaziridines were dosed at 1, 3 or $6 \times 10^{-4}$ M. Two BC-1 (tea stain) or EMPA 114 (red-wine) cloths each measuring 4×3 inches were used in the bleaching studies. Spaghetti sauce stained cloths were prepared by application of a tomato sauce extract to 4×6 inch cotton cloths. Two of these tomato-stained swatches were used in each oxaziridine bleach study. The amount of cloth bleaching was measured reflectometrically using a Colorgard System/05 Reflectometer. The test cloths were measured before and after washings. The amount of stain removal (i.e. color change with respect to P-Surf only) on BC-1 and EMPA 114 cloths is reported as $\Delta \Delta R$ whereas stain removal on the spaghetti stained cloths is reported as $\Delta \Delta B$. In general, an increase of 2 units of bleaching is perceivable to the human eye.

EXAMPLE 7

Table I illustrates the bleaching results on BC-1 cloth obtained from varying levels of oxaziridines (OX 11–16). These data were all accumulated at a wash pH of 9.5. Oxaziridine (OX 11), the parent compound, gave 4 to 5 units of bleaching on BC-1 stained cloth at concentrations between $1-6 \times 10^{-4}$M. Likewise, the relatively water-insoluble substrates OX 12 and 13 provided modest bleaching. The anticipated improved water solubility of the sulfoxide containing OX 14 was possibly responsible for the improved bleaching observed with this material. The cyclic oxaziridine, OX 16, also led to substantial bleaching at varying concentrations. Finally the heteroaromatic based OX 15 gave 15 units of bleaching at $6 \times 10^{-4}$M concentration; a quite impressive result. This substrate also demonstrated a significant amount of stain removal at 1 and $3 \times 10^{-4}$M.

TABLE I

| BC-1 Bleaching by Oxaziridines | | |
|---|---|---|
| OX | [OX] · $10^{-4}$M | $\Delta \Delta R$ |
| 11 | 6 | 5.0 |
|  | 3 | 4.5 |
|  | 1 | 4.0 |
| 12 | 3 | 2.4 |
|  | 1 | 1.8 |
| 13 | 6 | 3.0 |
| 14 | 6 | 7.5 |

TABLE I-continued

| BC-1 Bleaching by Oxaziridines | | |
|---|---|---|
| OX | $[OX] \times 10^{-4}M$ | ΔΔR |
|  | 3 | 6.3 |
|  | 1 | 4.6 |
| 15 | 6 | 15.3 |
|  | 3 | 11.0 |
|  | 1 | 5.1 |
| 16 | 6 | 7.7 |
|  | 3 | 4.9 |
|  | 1 | 2.9 |

OX 11 (dosed at $6 \times 10^{-4}M$) gave a R of 6 units on red-wine stained cloth (EMPA 114) at pH 9.5.

The bleaching of the hydrophobic spaghetti sauce stain was examined with OX 11 and 15 (see Table II). These data were obtained at a wash pH of 9.5. OX 11 provided a considerable amount of spaghetti stain removal at concentrations between $1-6 \times 10^{-4}M$. Analogously, OX 15 showed good ability to remove this hydrophobic stain. The amount of stain removal observed with these oxygen transfer agents was quite substantial when compared to peracids at pH 9.5.

TABLE II

| Spaghetti Stain Bleaching by Oxaziridines | | |
|---|---|---|
| OX | $[OX] \times 10^{-4}M$ | ΔΔB |
| 11 | 6 | 13.4 |
|  | 3 | 9.7 |
|  | 1 | 8.1 |
| 15 | 6 | 11.0 |
|  | 3 | 5.5 |
|  | 1 | 2.5 |

EXAMPLE 8

Fabric Bleaching by Oxaziridines (pH effects)

The effects were examined of pH on oxaziridine fabric bleaching. Tests were conducted in a terg-o-tometer as described above using BC-1 cloth. Table III lists the bleaching data obtained on OX 11 and 14 at pH levels between 8 and 10.5. Evidently the oxaziridine bleaching process is not influenced by pH since comparable levels of stain removal were observed at all pH levels studied. These results are in contrast to those obtained with peracids which typically give rise to lesser amounts of bleaching at higher pH levels. The pH independence of stain removal by oxaziridine can be quite advantageous where pH control is problematic.

TABLE III

| pH Effects on Oxaziridine BC1 Bleaching ($6 \times 10^{-4}M$ OX) | | |
|---|---|---|
| OX | pH | ΔR |
| 11 | 8 | 2.9 |
|  | 8.5 | 4.1 |
|  | 9 | 3.8 |
|  | 9.5 | 4.4 |
|  | 10 | 5.1 |
|  | 10.5 | 5.1 |
| 14 | 8 | 7.6 |
|  | 8.5 | 6.9 |
|  | 9 | 8.5 |
|  | 9.5 | 7.4 |
|  | 10 | 7.7 |
|  | 10.5 | 8.8 |

The foregoing description and Examples illustrate selected embodiments of the present invention. In light thereof, various modifications will be suggested to one skilled in the art all of which are within the spirit and purview of this invention.

What is claimed is:

1. A bleaching composition comprising:
   (i) from about 0.05 to about 10% of an oxygen transfer agent whose structure is:

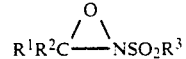

wherein:

$R^1$ may be a substituted or unsubstituted radical selected from the group consisting of hydrogen, phenyl, aryl, heterocyclic ring, alkyl and cycloalkyl radicals;

$R^2$ may be a substituted or unsubstituted radical selected from the group consisting of hydrogen, phenyl, aryl, heterocyclic ring, alkyl, cycloalkyl,

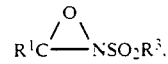

nitro, halo, cyano, alkoxy, keto, carboxylic, and carboalkoxy radicals;

$R^3$ may be a substituted or unsubstituted radical selected from the group consisting of phenyl, aryl, heterocyclic ring, alkyl, cycloalkyl, nitro, halo, and cyano radicals;

$R^1$ with $R^2$ and $R^2$ with $R^3$ may respectively together form a cycloalkyl, heterocyclic, and aromatic ring system; and (ii) from about 0.5 to 50% of a surfactant.

2. A composition according to claim 1 further comprising from about 1 to about 60% by weight of a peroxygen compound.

3. A composition according to claim 2 wherein the peroxygen compound is present in an amount from about 1.5 to 25% and the oxygen transfer agent is present in an amount from about 0.2 to 5% by weight.

4. A composition according to claim 2 wherein the peroxygen compound is an inorganic material selected from the group consisting of perborate, percarbonate, perphosphate, persilicate and monopersulphate salts.

5. A composition according to claim 2 wherein the peroxygen compound is an organic peroxyacid.

6. A composition according to claim 5 wherein the organic peroxyacid is selected from the group consisting of peracetic acid, monoperoxyphthalic acid and diperoxydodecanedioic acid.

7. A composition according to claim 6 wherein the monoperoxyphthalic acid is present as a magnesium salt hexahydrate.

8. A composition according to claim 2 further comprising a bleach precursor present in an amount such that the molar ratio of bleach precursor relative to oxygen transfer agent ranges from about 250:1 to about 1:20.

9. A composition according to claim 1 further comprising from about 1 to 80% of a detergent builder.

10. A composition according to claim 1 further comprising an effective amount for cleaning of an enzyme selected from the group consisting of proteases, cellulases, lipases, amylases and mixtures thereof.

11. A composition according to claim 1 delivered in a form selected from the group consisting of a powder, sheet, pouch, tablet, aqueous liquid and non-aqueous liquid.

12. A composition according to claim 1 wherein at least one of $R^1$, $R^2$ and $R^3$ is substituted with a water-solubilizing functional group.

13. A composition according to claim 12 wherein the water-solubilizing functional group is selected from the group consisting of carboxylic acid, phosphoric acid, phosphonic acid, sulfuric acid, sulphonic acid and salts thereof.

14. A composition according to claim 1 wherein said substituent on $R^1$, $R^2$ and $R^3$ is a functional unit selected from the group consisting of nitro, halo, cyano, $C_1$–$C_{20}$ alkyl, amino, aminoalkyl, thioalkyl, sulfoxyalkyl, carboxyester, hydroxy, $C_1$–$C_{20}$ alkoxy, polyalkoxy, $C_1$–$C_{40}$ quaternary di- or tri-alkylammonium functional units and mixtures thereof.

15. A composition according to claim 14 wherein said quaternary alkylammonium functional unit is a cholyl group.

16. A composition according to claim 1 wherein the oxygen transfer agent is 2-benzenesulfonyl-3-phenyloxaziridine.

17. A composition according to claim 1 wherein the oxygen transfer agent is 2-benzenesulfonyl-3-(4-nitrophenyl)oxaziridine.

18. A composition according to claim 1 wherein the oxygen transfer agent is 2-(4-chlorobenzenesulfonyl)-3-(4-chlorophenyl)oxaziridine.

19. A composition according to claim 1 wherein the oxygen transfer agent is 2-benzenesulfonyl-3-(4-methylsulfonylphenyl)oxaziridine.

20. A composition according to claim 1 wherein the oxygen transfer agent is 3-butyl-1,2-benzisothiazole-1,1-dioxide Oxide.

21. A composition according to claim 1 wherein the oxygen transfer agent is 2-benzenesulfonyl-3-(3-pyridinyl)oxaziridine.

22. A method for bleaching a stained substrate, said method comprising contacting said stained substrate in an aqueous medium with an oxygen transfer agent whose structure is:

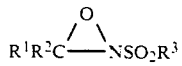

wherein:
$R^1$ may be a substituted or unsubstituted radical selected from the group consisting of hydrogen, phenyl, aryl, heterocyclic ring, alkyl and cycloalkyl radicals;
$R^2$ may be a substituted or unsubstituted radical selected from the group consisting of hydrogen, phenyl, aryl, heterocyclic ring, alkyl, cycloakyl,

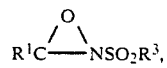

nitro, halo, cyano, alkoxy, keto, carboxylic and carboalkoxy radicals;
$R^3$ may be a substituted or unsubstituted radical selected from the group consisting of phenyl, aryl, heterocyclic ring, alkyl, cycloalkyl, nitro, halo, and cyano radicals;
$R^1$ with $R^2$ and $R^2$ with $R^3$ may respectively together form a cycloalkyl, heterocyclic, and aromatic ring system.

23. A method according to claim 22 wherein the aqueous medium further comprises a peroxygen compound and the molar ratio of peroxygen compound to oxygen transfer agent ranges from about 1500:1 to 1:2.

24. A method according to claim 23 wherein the aqueous medium further comprises a bleach precursor and the molar ratio of a bleach precursor to oxygen transfer agent ranges from about 250:1 to about 1:20.

25. A method for bleaching a stained substrate, said method comprising contacting said stained substrate in an aqueous medium with a surfactant and with an oxygen transfer agent whose structure is:

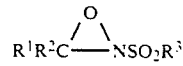

wherein:
$R^1$ may be a substituted or unsubstituted radical selected from the group consisting of hydrogen, phenyl, aryl, heterocyclic ring, alkyl and cycloalkyl radicals;
$R^2$ may be a substituted or unsubstituted radical selected from the group consisting of hydrogen, phenyl, aryl, heterocyclic ring, alkyl, cycloalkyl,

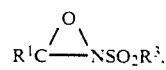

nitro, halo, cyano, alkoxy, keto, carboxylic and carboalkoxy radicals;
$R^3$ may be a substituted or unsubstituted radical selected from the group consisting of phenyl, aryl, heterocyclic ring, alkyl, cycloalkyl, nitro, halo, and cyano radicals;
$R^1$ with $R^2$ and $R^2$ with $R^3$ may respectively together form a cycloalkyl, heterocyclic, and aromatic ring system; and said contacting occurring in said medium containing surfactant of about 0.05 to 1.0 grams per liter and oxygen oxygen transfer agent in an amount of about 0.01 to about 300 ppm per liter of medium.

26. A method according to claim 25 wherein said liquid medium comprises surfactant in an amount from about 0.15 to about 0.40 grams per liter and oxygen transfer agent in an amount of from about 5 to about 100 ppm per liter of medium.

27. A method according to claim 24 wherein the molar ratio of peroxygen compound to oxygen transfer agent ranges from about 150:1 to about 1:1 and the molar ratio of bleach precursor to oxygen transfer agent ranges from about 100:1 to about 1:1.

28. A method according to claim 22 wherein said substrate is selected from the group consisting of fabrics, household fixtures and tableware.

29. A method according to claim 22 wherein said substrate is a denture.

* * * * *